| United States Patent [19] | [11] Patent Number: 5,037,376 |
| Richmond et al. | [45] Date of Patent: Aug. 6, 1991 |

[54] APPARATUS AND METHOD FOR TRANSMITTING PROSTHETIC INFORMATION TO THE BRAIN

[75] Inventors: Barry J. Richmond, Bethesda; Lance M. Optican, Potomac, both of Md.

[73] Assignee: The United States of America as represented by the Department of Health and Human Services, Washington, D.C.

[21] Appl. No.: 222,882

[22] Filed: Jul. 22, 1988

[51] Int. Cl.$^5$ ............................................. A61M 21/00
[52] U.S. Cl. ...................................... 600/26; 128/897; 623/24
[58] Field of Search .................... 623/24, 25; 128/897, 128/898, 420.5; 600/26-28

[56] References Cited

PUBLICATIONS

Richmond, B. J. and L. M. Optican, (1986), "Temporal Encoding of Pictures by Striate Neuronal Spike Trains. I. The Multiplex-Filter Hypothesis." *Society for Neuroscience*, Abstract 12:431.

Optican, L. M. and B. J. Richmond, (1986), "The Temporal Encoding of Pictures by Striate Neuronal Spike Trains. II. Predicting Complex Cell Responses." *Society for Neuroscience*, Abstract 12:431.

*Primary Examiner*—Kyle L. Howell
*Assistant Examiner*—J. P. Lacyk
*Attorney, Agent, or Firm*—Cushman, Darby & Cushman

[57] ABSTRACT

An apparatus and method for transmitting prosthetic information to the brain contains an array of sensory elements that receive energy from an external stimulus and process those signals via neural filters and neural waveforms to produce a pulse or 'spike' train that is temporally encoded with information that is functionally related to the external stimulus. The simulated spike trains, when applied to an appropriate area of the brain, produce perceptions that are functionally related to the sensed external stimuli so that a subject can discriminate between different spike trains representative of different external stimuli.

24 Claims, 9 Drawing Sheets

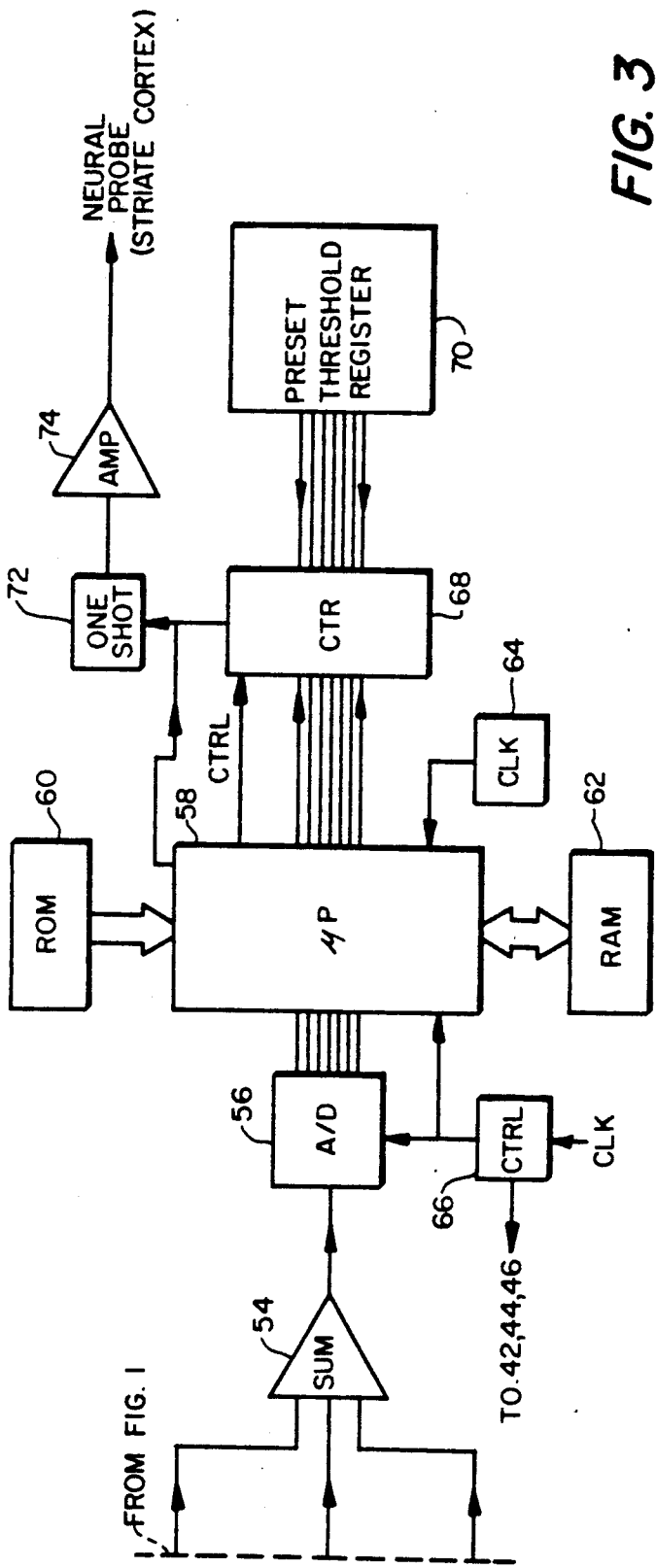

| TIME(ms) | VALUE |
|---|---|
| 0 | 0.0443110 |
| 5 | 0.0753230 |
| 10 | 0.1170940 |
| 15 | 0.1632160 |
| 20 | 0.2041640 |
| 25 | 0.2312780 |
| 30 | 0.2403380 |
| 35 | 0.2327660 |
| 40 | 0.2138700 |
| 45 | 0.1901990 |
| 50 | 0.1671190 |
| 55 | 0.1478710 |
| 60 | 0.1337540 |
| 65 | 0.1247830 |
| 70 | 0.1202900 |
| 75 | 0.1192430 |
| 80 | 0.1204720 |
| 85 | 0.1226630 |
| 90 | 0.1247080 |
| 95 | 0.1259050 |
| 100 | 0.1261860 |
| 105 | 0.1257600 |
| 110 | 0.1248300 |
| 115 | 0.1233810 |
| 120 | 0.1214200 |
| 125 | 0.1191800 |
| 130 | 0.1170440 |
| 135 | 0.1153290 |
| 140 | 0.1138810 |
| 145 | 0.1122680 |
| 150 | 0.1103080 |
| 155 | 0.1082660 |
| 160 | 0.1064810 |
| 165 | 0.1049240 |
| 170 | 0.1032050 |
| 175 | 0.1010860 |
| 180 | 0.0987560 |
| 185 | 0.0966750 |
| 190 | 0.0951690 |
| 195 | 0.0942760 |
| 200 | 0.0937720 |
| 205 | 0.0933940 |
| 210 | 0.0929080 |
| 215 | 0.0921320 |
| 220 | 0.0910240 |
| 225 | 0.0896700 |
| 230 | 0.0882570 |
| 235 | 0.0870030 |
| 240 | 0.0860130 |
| 245 | 0.0851340 |
| 250 | 0.0841740 |
| 255 | 0.0830530 |
| 260 | 0.0819270 |
| 265 | 0.0809990 |
| 270 | 0.0803430 |
| 275 | 0.0798240 |
| 280 | 0.0793820 |
| 285 | 0.0790450 |
| 290 | 0.0787980 |
| 295 | 0.0783580 |
| 300 | 0.0772410 |
| 305 | 0.0751700 |
| 310 | 0.0722010 |
| 315 | 0.0687870 |

| TIME (ms) | VALUE |
|---|---|
| 0 | 0.0834020 |
| 5 | 0.1409390 |
| 10 | 0.2076300 |
| 15 | 0.2662960 |
| 20 | 0.2995730 |
| 25 | 0.2982760 |
| 30 | 0.2648230 |
| 35 | 0.2102740 |
| 40 | 0.1482040 |
| 45 | 0.0894680 |
| 50 | 0.0403130 |
| 55 | 0.0027080 |
| 60 | -0.0240520 |
| 65 | -0.0417880 |
| 70 | -0.0525610 |
| 75 | -0.0584730 |
| 80 | 0.0616610 |
| 85 | -0.0640590 |
| 90 | -0.0670390 |
| 95 | -0.0707800 |
| 100 | -0.0747410 |
| 105 | -0.0783210 |
| 110 | -0.0813300 |
| 115 | -0.0838470 |
| 120 | -0.0857630 |
| 125 | -0.0867970 |
| 130 | -0.0869870 |
| 135 | -0.0868480 |
| 140 | -0.0868450 |
| 145 | -0.0868750 |
| 150 | -0.0863130 |
| 155 | -0.0847000 |
| 160 | -0.0822130 |
| 165 | -0.0794450 |
| 170 | -0.0770480 |
| 175 | -0.0755010 |
| 180 | -0.0751240 |
| 185 | -0.0759200 |
| 190 | -0.0775990 |
| 195 | -0.0795150 |
| 200 | -0.0809070 |
| 205 | -0.0811940 |
| 210 | -0.0802140 |
| 215 | -0.0784800 |
| 220 | -0.0768480 |
| 225 | -0.0760120 |
| 230 | -0.0758960 |
| 235 | -0.0758870 |
| 240 | -0.0753500 |
| 245 | -0.0741620 |
| 250 | -0.0727020 |
| 255 | -0.0714120 |
| 260 | -0.0705010 |
| 265 | -0.0696150 |
| 270 | -0.0681390 |
| 275 | -0.0656960 |
| 280 | -0.0626150 |
| 285 | -0.0597700 |
| 290 | -0.0579760 |
| 295 | -0.0572640 |
| 300 | -0.0568420 |
| 305 | -0.0557990 |
| 310 | -0.0535720 |
| 315 | -0.0502330 |

| TIME (ms) | VALUE |
|---|---|
| 0 | 0.0994760 |
| 5 | 0.1402630 |
| 10 | 0.1676830 |
| 15 | 0.1638380 |
| 20 | 0.1216490 |
| 25 | 0.0499750 |
| 30 | -0.0311940 |
| 35 | -0.1011310 |
| 40 | -0.1475100 |
| 45 | -0.1690590 |
| 50 | -0.1718990 |
| 55 | -0.1640830 |
| 60 | -0.1516910 |
| 65 | -0.1381650 |
| 70 | -0.1257560 |
| 75 | -0.1158630 |
| 80 | -0.1086250 |
| 85 | -0.1027740 |
| 90 | -0.0964920 |
| 95 | -0.0887020 |
| 100 | -0.0794260 |
| 105 | -0.0693570 |
| 110 | -0.0593190 |
| 115 | -0.0501140 |
| 120 | -0.0420100 |
| 125 | -0.0344360 |
| 130 | -0.0264240 |
| 135 | -0.0176150 |
| 140 | -0.0085510 |
| 145 | 0.0004030 |
| 150 | 0.0095770 |
| 155 | 0.0194610 |
| 160 | 0.0297030 |
| 165 | 0.0390350 |
| 170 | 0.0463420 |
| 175 | 0.0515310 |
| 180 | 0.0555400 |
| 185 | 0.0594000 |
| 190 | 0.0637840 |
| 195 | 0.0689570 |
| 200 | 0.0749680 |
| 205 | 0.0814380 |
| 210 | 0.0875220 |
| 215 | 0.0922280 |
| 220 | 0.0950710 |
| 225 | 0.0963460 |
| 230 | 0.0969210 |
| 235 | 0.0978230 |
| 240 | 0.0995210 |
| 245 | 0.1018150 |
| 250 | 0.1041270 |
| 255 | 0.1061120 |
| 260 | 0.1078720 |
| 265 | 0.1095030 |
| 270 | 0.1107770 |
| 275 | 0.1113810 |
| 280 | 0.1112050 |
| 285 | 0.1103960 |
| 290 | 0.1089000 |
| 295 | 0.1062970 |
| 300 | 0.1019720 |
| 305 | 0.0957650 |
| 310 | 0.0881450 |
| 315 | 0.0800220 |

APPARATUS AND METHOD FOR TRANSMITTING PROSTHETIC INFORMATION TO THE BRAIN

BACKGROUND OF THE INVENTION

The present invention relates to transmission of sensory information obtained by a prosthetic device to the brain to create a sensory perception. In particular, the present invention relates to the transmission of visual, audile, or tactile information to the brain in an encoded form that causes a functionally related perception on the part of the subject.

In normal circumstances, a healthy human being receives a stimulus from the external environment that is detected by the appropriate type of receptor. For example, photoreceptors within the eye detect light with each photoreceptor converting the received stimulus into neuron impulses. This conversion of the stimulus energy into neuron impulses takes place in one or more neurons that are associated with the receptor. Each neuron then emits a neuron spike sequence that is used by the brain to obtain sensory perception. The combination of many neurons, each transmitting many neuron spike trains provide a complete or global sensory perception.

It is known that a simulated neuron spike or pulse train can produce a sensory perception in a subject when applied to selected areas of the brain, spinal column, or nerves of a subject. Additionally, the brain has been 'mapped' so that specific locations on or within the brain are associated with specific sensory perceptions. Placement of an electrode at an appropriate location and stimulation with electrical pulses will produce a sensory perception. For example, an electrode placed on the striate cortex and to which a simulated neuron impulse train is transmitted will cause some type of visual perception.

Repeated pulses to a specific location, such as the striate cortex, will produce some type of perceivable image. However, meaningful information as to form, luminescence, and color is not conveyed. It is presently believed that the informational content for all dimensions of a sense have their basis in a coding scheme that is based upon the number of neuron impulses that occur during a predetermined interval, for example, a greater number of neuron impulses are believed to be a function of a more intense perceived parameter. However, this coding scheme only allows one dimension of a sense to be coded by each neuron. Proponents of this coding scheme believe that the large number of neurons contain a distribution among them that allows the various dimensions of sense to be recognized so that perception can take place. However, it has not been possible to determine how these various dimensions are recognized using this population coding scheme. It has not been possible to develop a prosthetic device using this population coding principle which can sense an external stimulus and transmit information to the brain so that meaningful sensory perception can take place.

SUMMARY OF THE INVENTION

In view of the above, it is an object of the present invention, among others, to provide an apparatus and method for transmitting prosthetic information to the brain.

It is another object of the present invention to provide an apparatus and method that will allow meaningful encoding of visual, audile, or tactile sensory information.

It is still another object of the present invention to provide an apparatus and method to produce simulated neural impulse trains that replicate the neural impulse trains produced naturally by neurons in the body.

In view of these objects, and others, the present invention provides an apparatus and method for transmitting prosthetic information to the brain in the form of simulated neuron impulse trains that contain a time varying component. This time varying component corresponds to the time varying component that exists within natural neuron impulse trains allows information concerning multiple dimensions of a sense to be contained in the simulated neuron impulse train.

The apparatus and method of the present invention sense an external stimulus with an array of sensors. The output of each of these sensors is used to determine simulated neuron impulse trains associated with each sensor. Each sensor acts as a channel that sends its simulated neuron impulse trains to the appropriate sensory location so that the sense can be perceived. The array of channels transmits simulated neuron impulse trains in parallel to allow sensory perception.

The present invention utilizes a series of characteristic sensory functions in combination with respective temporal neural filters. Processing of sensory perceived parameters via these characteristic functions and neural filters results in simulated neural impulse trains, or spike trains, containing the properly time varying components that allow the brain to sense the external stimulus. The natural encoding method of the simulated spike trains allows the brain's intrinsic mechanisms to interpret their meaning.

The present invention advantageously allows a person to perceive environmental parameters, such as light, sound, or touch, via simulated neural spike trains that emulate naturally occurring spike trains with a temporal modulation scheme in such a way that the perception based on the simulated spike train will be functionally related to the external stimuli or parameter.

Other objects and further scope of applicability of the present invention will become apparent from the detailed description to follow, taken in conjunction with the accompanying drawings, in which like parts are designated by like reference characters.

BRIEF DESCRIPTION OF THE DRAWING

FIG. 2 is a partial schematic block diagram of the system of the present invention;

FIG. 3 is a legend indicating the manner by which FIGS. 1 and 2 are to be read;

DESCRIPTION OF THE PREFERRED EMBODIMENT

Figure 1:
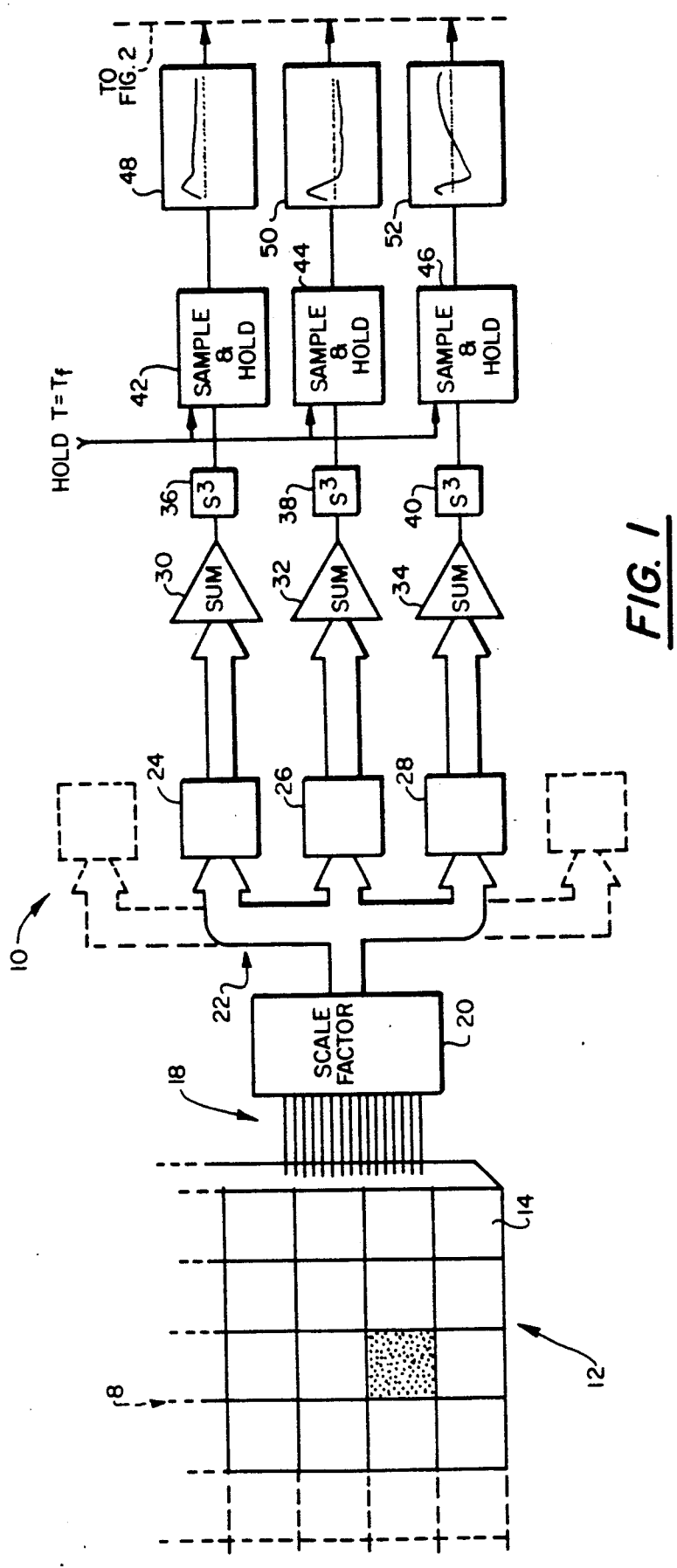
FIG. 1 is a partial schematic block diagram of a system for generating a simulated neural impulse train for stimulating the visual cortex of the human brain.

An exemplary system in accordance with the present invention for generating simulated neural impulses from an environmental parameter and providing a functionally related 'spike' train for stimulating the brain to effect a functionally related perception of the environmental parameter is shown in FIGS. 1 and 2 and is designated generally therein by the reference character 10. The system 10 is designed to sense an environmental parameter in the form of variations in light that define an image and provide a corresponding spike train that is temporally modulated, i.e., pulse position modulated, and which, when used to stimulate a portion of the brain of a subject, produces a perception that is functionally related to the sensed light or image. As shown in FIG. 1, the exemplary embodiment of the system 10 includes an array 8 of individual photoreceptors 14. In FIG. 1, sixteen photoreceptors 14 are shown in solid-line illustration and represent an input sub-array 12 for one sub-image information channel for transducing environmental light into corresponding electrical signals presented on respective output lines, indicated generally at 18. As can be appreciated, other photoreceptors 14 are similarly arrayed as the input transducers for other sub-image information channels (not specifically shown in FIGS. 1 and 2) so that a multi-channel system is provided to effectively assemble a set of output spike trains that are representative of the image sensed by the input sub-array 12. The photoreceptors 14 can be individual planar photocells, photodiodes, or phototransistors arranged in an array or can take the form of a subset of the photoreceptors on a planar integrated device. If desired, an optical system can be provided to image subjects of principal and secondary interest within a selected field of view onto the array 12.

A scale-factor conditioner 20 is provided to accept the outputs of the input sub-array 12 and introduce a scaling factor that is a function of the light-to-signal input/output function of the particular photoreceptors 14. The scaling factors are determined empirically and vary, for example, as a function of the sensitivity and spectral response of the particular photoreceptors 14. In addition, the scale-factor conditioner 20 can introduce a logarithmic function (typically $\log_e$) to compensate for the functional response characteristics of the photoreceptors 14. Where the input sub-array 12 is part of a scanning camera, for example, the camera typically provides the logarithmic function compensation.

The appropriately scaled output of the scale-factor conditioner 20 is provided via an appropriate bus 22 connection to each of three signal-weighting filters 24, 26, and 28. Each of the signal-weighting filters accepts all the scale-factored signal outputs of the scale-factor conditioner 20 and multiplies the respective outputs by a specific weighting value to provide a spatial filter effect that is related to respective neural transforms described more fully below. For the sixteen signal lines of the input sub-array 12, weight values for the signal-weighting filters 24, 26, and 28 for the preferred embodiment are as listed, respectively, in Tables I, II, and III below and presented in the four-by-four array format corresponding to the input sub-array 12.

TABLE I

| | | | |
|---|---|---|---|
| −0.423000 | −0.004000 | −0.118000 | −0.099000 |
| −0.329000 | 3.366000 | 0.888000 | −0.285000 |
| 0.343000 | 8.327000 | 1.527000 | −0.297000 |
| −0.287000 | −0.706000 | −0.210000 | −0.474000 |

TABLE II

| | | | |
|---|---|---|---|
| −0.028300 | −0.139600 | −0.029400 | −0.178400 |
| −0.377900 | −0.725700 | −0.243300 | 0.083600 |
| −0.273900 | 1.861400 | −0.184400 | −0.168000 |
| −0.156200 | −0.367900 | −0.218200 | −0.185200 |

TABLE III

| | | | |
|---|---|---|---|
| −0.028640 | 0.128490 | 0.155270 | −0.033330 |
| 0.108840 | 0.159940 | 0.183120 | 0.350690 |
| −0.081850 | 0.212080 | 0.082500 | −0.007050 |
| −0.066830 | −0.180620 | −0.005260 | 0.068260 |

The values for the three signal-weighting filters 24, 26, and 28 in Tables I, II and III were determined empirically from the analysis of physiological data. In general, the set of signal-weighting filters must be chosen to form a mathematical basis for representing the image falling on the sensor array 12. The resolution of this channel is controlled by the number of photoreceptors 14 within the input sub-array 12 and the number signal-weighting filters.

After the signal weighting is effected by the signal-weighting filters 24, 26, and 28, the respective outputs are provided to summing amplifiers 30, 32, and 34, which sum the individual weighted inputs to provide a single respective scalar output S that is provided to respective cubic function (i.e., $S^3 = aS^3 + bS^2 + cS + d$) generators 36, 38, and 40 that scale each signal in a non-linear manner to compensate for low input signal values. The summing amplifiers can be fabricated from conventional operational amplifiers configured in a summing mode, and the cubic function generators 36, 38, and 40 can be fabricated from conventional analog multiplier devices.

Sample-and-hold circuits 42, 44, and 46 are provided respectively at the outputs of the cubic function generators 36, 38, and 40 and are designed to continuously sample the output voltage values. The system 10 is designed to generate output simulated neural impulses on a frame-by-frame basis, with the simulated neural impulses generated subsequent to each frame and prior to the subsequent frame. A frame is terminated on a system-wide basis by a timing signal $T = T_f$ which, when applied to the sample-and-hold circuits 42, 44, and 46, causes the respective circuit to store the signal value at its input for subsequent processing as explained below. Each sample-and-hold circuit 42, 44, 46 can be defined by a series-connected capacitor and switch, such as a MOSFET.

Neural transform function units 48, 50, and 52 are provided, respectively, at the outputs of the sample-and-hold circuits 42, 44, and 46. Each neural transform function unit 48, 50, and 52 includes an empirically determined, time-dependent neural transfer function that is multiplied by the value stored in the respective sample-and-hold circuits 42, 44, and 46. The transforms are determined by measuring biological neuron responses to mathematically complete sets of stimuli, e.g., Walsh patterns. It has been empirically determined that the transfer functions presented in neural transform function units 48, 50, and 52 are a statistically valid analog of actual neural responses. These waveforms, along with the corresponding three signal-weighting filters 24, 26, and 28, thus allow the system 10 to generate simulated neural impulses for use in stimulating the visual cortex of the brain.

Figures 4, 5:
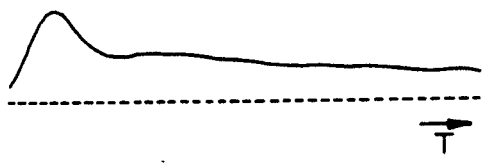
FIG. 4 is a graphical illustration of a first neural transform in which the abscissa represents time and the ordinate represents magnitude.
FIG. 5 is a table providing quantitative data as to the neural transform of FIG. 4 in which the left column represents time in milliseconds from zero to 315 ms. and the right column presents the corresponding magnitude value.
Figures 6, 7:
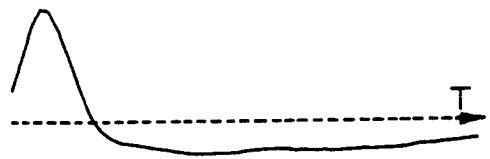
FIG. 6 is a graphical illustration of a second neural transform in which the abscissa represents time and the ordinate represents magnitude.
FIG. 7 is a table providing quantitative data as to the neural transform of FIG. 6 in which the left column represents time in milliseconds from zero to 315 ms. and the right column presents the corresponding magnitude value.
Figures 8, 9:
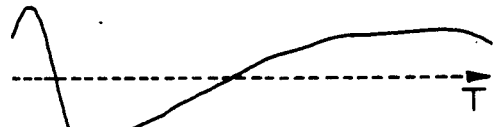
FIG. 8 is a graphical illustration of a third neural transform in which the abscissa represents time and the ordinate represents magnitude.
FIG. 9 is a table providing quantitative data as to the neural transform of FIG. 8 in which the left column represents time in milliseconds from zero to 315 ms. and the right column presents the corresponding magnitude value.

The neural waveform for the neural waveform unit 48 is reproduced on an enlarged scale in FIG. 4 in which the abscissa represents time, and the ordinate represents magnitude. The neural waveform of FIG. 4 is also presented in a quantitative manner in FIG. 5 with the left column representing time in milliseconds between zero and 315 ms. and the right column representing the corresponding magnitude. In a similar manner, the neural waveform of neural transform function units 50 and 52 are shown in enlarged scale in FIGS. 6 and 8, respectively, and their quantitative data in FIGS. 7 and 9. These examples of neural transform function units 48, 50, and 52 were determined empirically from the analysis of physiological data. The number of waveforms is determined by the number of signal-weighting filters with three exemplary signal-weighting filters 24, 26, and 28 shown in FIG. 1. As represented by the dotted-line extension of bus 22 in FIG. 1 and the dotted-line blocks above and below the signal-weighting filters 24 and 28, the number of signal-weighting filters may vary depending upon the desired resolution, as long as each signal-weighting filter is mathematically orthogonal. While 64 time and corresponding data values are shown in FIGS. 5, 7, and 9, it is preferred that data values at one millisecond intervals be utilized in the signal processing, these values provided by interpolation of the data values presented in FIGS. 5, 7, and 9.

Further disclosure regarding the neural waveforms and the neuro-physiology of the present invention is provided in the following publications, the disclosures of which are incorporated herein by reference: Richmond, B. J., L. M. Optican, M. Podell, and H. Spitzer (Jan., 1987) "Temporal encoding of two-dimensional patterns by single units in primate inferior temporal cortex; I. Response characteristics." *J. Neurophysiol.* vol. 57:132–146; Richmond, B. J. and L. M. Optican (Jan., 1987) "Temporal encoding of two-dimensional patterns by single units in primate inferior temporal cortex; II. Quantification of response waveform." *J. Neurophysiol.* vol. 57:147–161; Optican, L. M. and B. J. Richmond (Jan., 1987) "Temporal encoding of two-dimensional patterns by single units in primate inferior temporal cortex. III. Information theoretic analysis." *J. Neurophysiol.* vol. 57:162–178; Richmond, B. J. and L. M. Optican (1986) "Temporal encoding of pictures by striate neuronal spike trains. I. The multiplex-filter hypothesis." *Society for Neuroscience*, Abstract 12:431; Optican, L. M. and B. J. Richmond (1986) "Temporal encoding of pictures by striate neuronal spike trains. II. Predicting complex cell responses." *Society for Neuroscience*, Abstract 12:431.

Once the time-dependent neural transfer functions in the neural waveform function units 48, 50, and 52 are multiplied by the values stored in the respective sample-and-hold circuits 42, 44, and 46, the products are summed in a summing amplifier 54 to provide a time-varying output that is related to the image sensed by the input sub-array 12. The output of the summing amplifier 54 is provided to an analog-to-digital converter 56 to provide a digitized output thereof for subsequent conversion into a spike train as explained more fully below.

Figure 10:
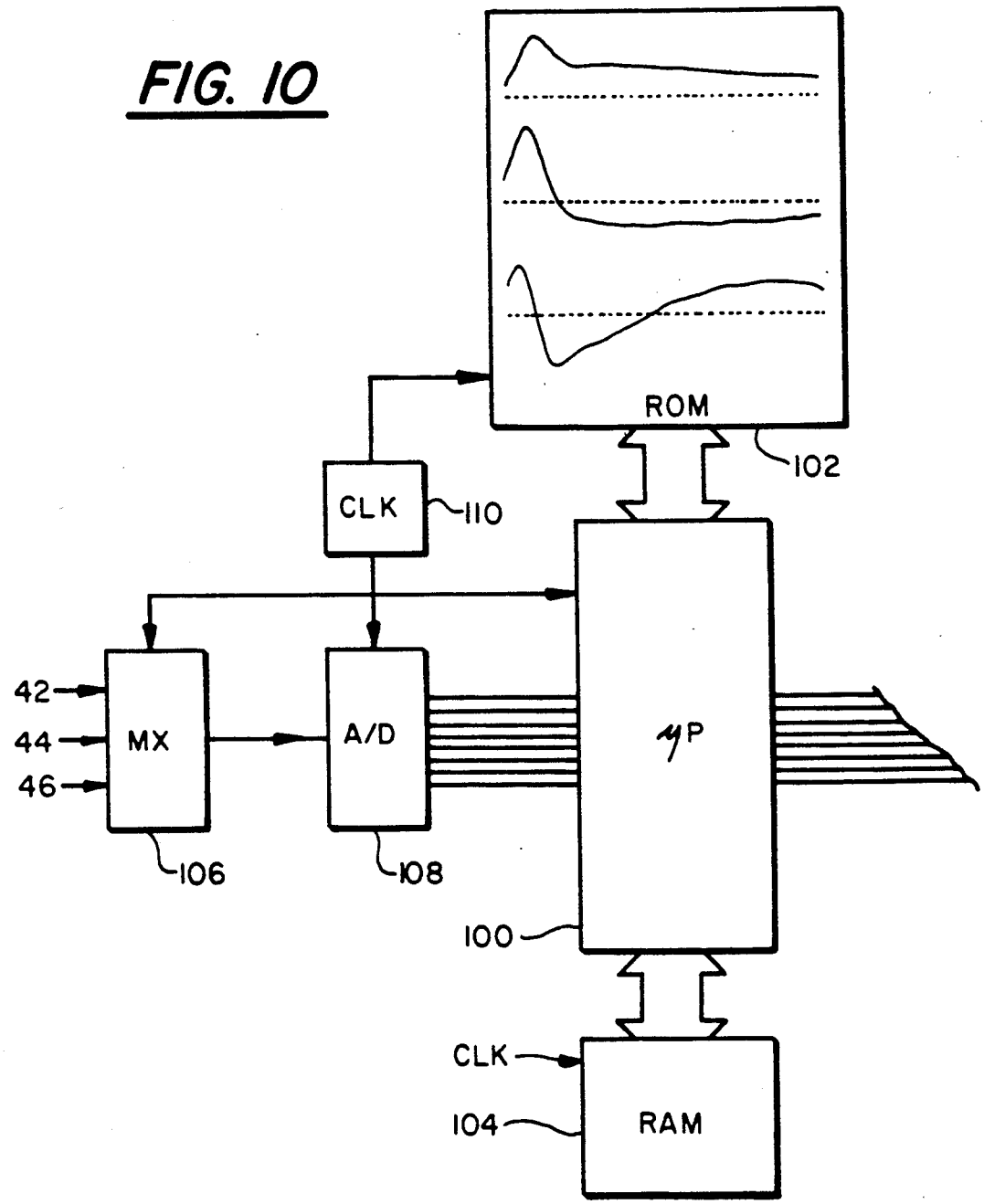
FIG. 10 is a schematic block diagram of a stored-program controlled processor for effecting various transformations in a digital manner.

The neural transform function units 48, 50, and 52 are shown in functional block form in FIGS. 1 and 2 and are preferably implemented in a digital manner with a stored-program controlled processor. For example and as shown in FIG. 10, the functions performed by the neural waveform units 48, 50, and 52 and the summing amplifier 54 are performed by a microprocessor 100 that is coupled to a read-only-memory (ROM) 102 and a random-access-memory (RAM) 104. A multiplexer 106 accepts the inputs from the sample-and-hold circuits 42, 44, and 46 and, in response to appropriate 'select' signals, provides the selected sample-and-hold value to an analog-to-digital (A/D) converter 108 which, in turn provides the corresponding digitized sample-and-hold value to the microprocessor 100. A clock 110 provides the necessary timing and control signals to the various devices to effect synchronized operation.

The ROM 102 includes the data tables of FIGS. 5, 7, and 9. The clock 110 provides the timing and control signal to the multiplexer 106 to select one of the sample-and-hold values which is digitized and stored in one of the general purpose registers in the microprocessor 100 with the procedure repeated until three digital values representative of the three sample-and-hold values are stored in digital form. The microprocessor 100 then reads the first time value (i.e., t=0 ms.) from the ROM 102 for a first of the neural waveforms and effects a multiplication by the corresponding digitized value in sample-and-hold 42 and stores the respective product temporarily in the RAM 104. In a similar manner, the first values for the second and the successive neural waveforms are obtained from the ROM 102, multiplied by their corresponding value from their respective sample-and-hold circuits, and the products stored. The three products are then digitally summed and the results again stored. The second time value for the various neural waveforms are then obtained, multiplied by their respective digital sample-and-hold values, and the sum thereof stored in the RAM 104. As can be appreciated, the process is repeated in a recurring manner until a set of output values is obtained that corresponds to the output of the analog-to-digital converter 56 of the functional block diagram of FIGS. 1 and 2. Hence, FIG. 10 provides a circuit that implements functional blocks 48, 50, 52, 54, and 56 of FIGS. 1 and 2.

Once the neural waveforms are multiplied by their respective sample-and-hold values and the products summed and digitized, as shown in functional form in FIGS. 1 and 2 or by the processor-implemented form in FIG. 10, the digital output is converted to a spike train the spacing of which encodes information functionally related to that sensed by the input sub-array 12. As shown in FIG. 2, the digital output of the analog-to-digital converter 56, which represents a succession of digital values representative of the processed neural waveform values, is presented to a stored-program controlled microprocessor 58 that is coupled to read-only-memory (ROM) 60 that contains a program sequence, as presented in FIG. 11, and a random-access-memory (RAM) 62 for storing various intermediate and other values. A clock 64 provides timing pulses while a controller 66 provides the necessary select, enable, and control signals to provide synchronous operation of the various devices. The microprocessor 58 is coupled, along with appropriate control lines, to a counter 68 that is periodically parallel-loaded with a preset threshold value X from a register 70. The output of the counter 68 is provided to a one-shot monostable multivibrator 72 that provides, in response to an appropriate trigger signal, a pulse or spike of selected pulse amplitude and duration. As explained below, a succession of such spikes are provided with an inter-spike temporal spacing that contains the encoded information from the image sensed by the input sub-array 12. The output of the one-shot nonstable multivibration 72 is provided through a conditioning amplifier 74 which controls the voltage output to provide a spike train of appropriate voltage level (typically 10 to 500 microvolts with a 50 to 100 microsecond spike width duration) for stimulating the appropriate spot or area of the visual cortex.

Figure 11:
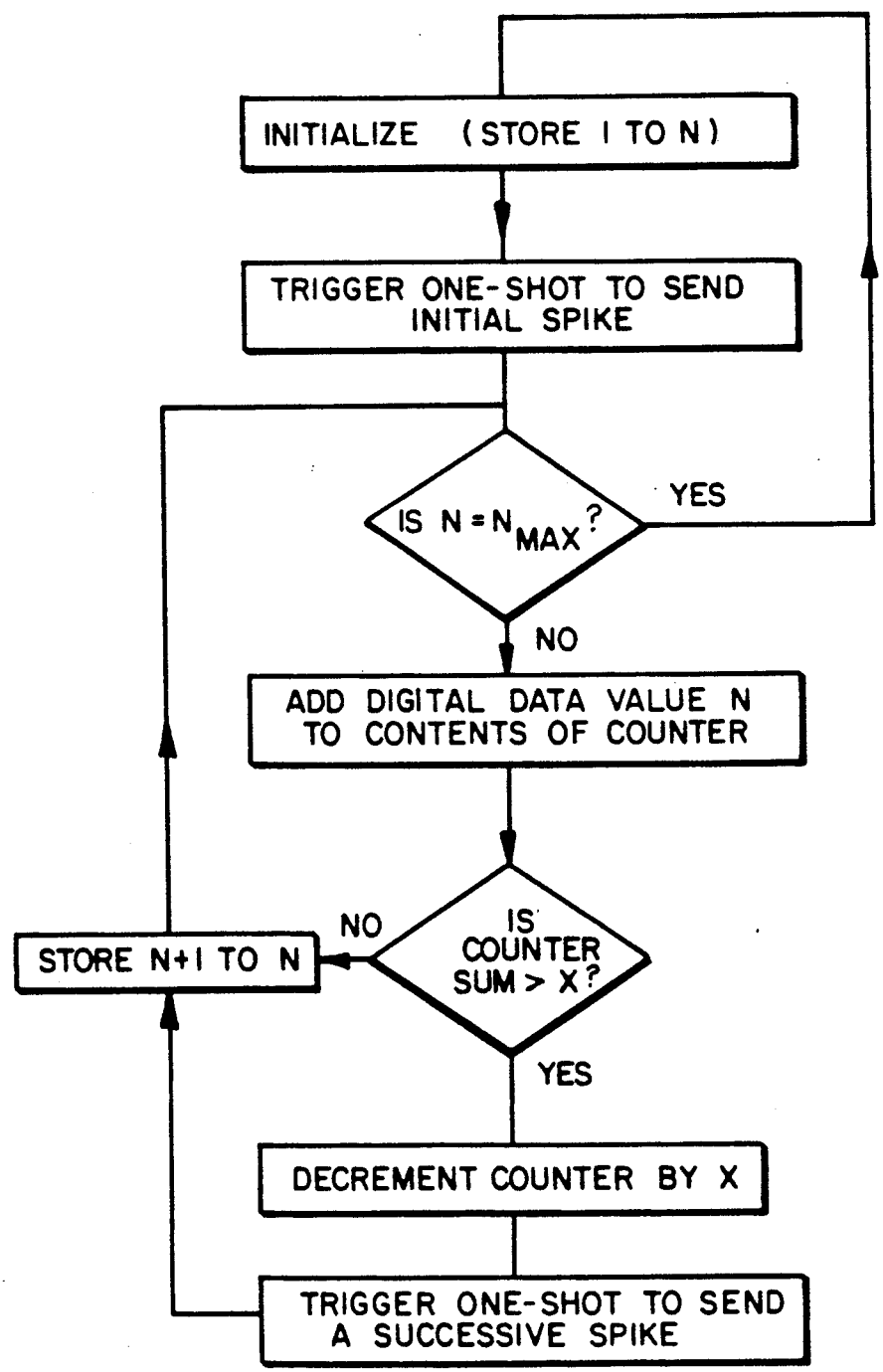
FIG. 11 is a flow diagram illustrating a control sequence for converting digital values into a temporally modulated spike train suitable for stimulating the striate cortex to effect a visual perception in a subject.

The microprocessor 58 of FIG. 2 operates in accordance with the control sequence of FIG. 11 to produce a temporally modulated spike train as a function of the digital values presented from the analog-to-digital converter 56. As shown in FIG. 11, the system initializes, in part, by storing 1 to the data pointer variable, N, with N having a maximum value $N_{max}$ that represents the total number of digital data values for that frame and which must be converted into a spike train representative of that frame. For example, a frame can be represented by $N_{max}=300$ digital values determined by interpolation of the 64 time values shown in FIGS. 5, 7, and 9, each value of which is the sum of the products of the corresponding values of the neural waveforms (FIGS. 4–9) and the sample-and-hold values.

After initialization, the one-shot 72 is triggered to provide an initial spike, having a pulse duration or spike width of between 50 and 100 microseconds and a selected voltage amplitude. A query is presented to determine if all the digital data values for a frame have been processed, i.e., if $N=N_{max}$, and, if so, the control returns to re-initialize for the next frame. If less than all the digital data values have been processed, the $N^{th}$ digital data value is added to the contents of the counter 68. A query is presented to determine if the accumulated contents of the counter 68 are greater than a selected value X (e.g., 1000), and, if not, the data pointer N is incremented by 1 and the program loops to add the next data value to the counter 68, provided that N is not equal to $N_{max}$. If the counter sum is greater than X, the counter is decremented by X by effecting a parallel load from the register 70, and, substantially concurrently, triggering the one-shot 72 to produce the next successive spike. Thereafter, the data pointer N is incremented by one with the program looping to continue to successively add the digital data values to the counter 68, decrement by X when X is exceeded, and issue the next successive spike. As can be appreciated, the time duration between each spike is a function of the rate at which the digital value accumulates to exceed X so that a temporally modulated spike train is generated, i.e., a spike train in which the inter-spike timing is varied as a function of the products of the corresponding values of the neural waveforms (FIGS. 4–9) with the sample-and-hold values that are a function of the image sensed by the input sub-array 12.

The spike train output of the one-shot 72 is provided to an amplifier 74 which provides a buffered output, typically no more than 10–100 microvolts, that is provided to a neural probe that is placed in a selected location on an appropriately mapped visual cortex of the brain of a subject to stimulate a neuron(s) to cause perception of an image or light pattern that is functionally related to that sensed by the input sub-array 12. The other adjacent channels (not specifically shown in FIGS. 1 and 2) similarly drive other neural electrodes placed in an electrode grid pattern corresponding to the visual maps of the entire input array 8.

Figure 12:
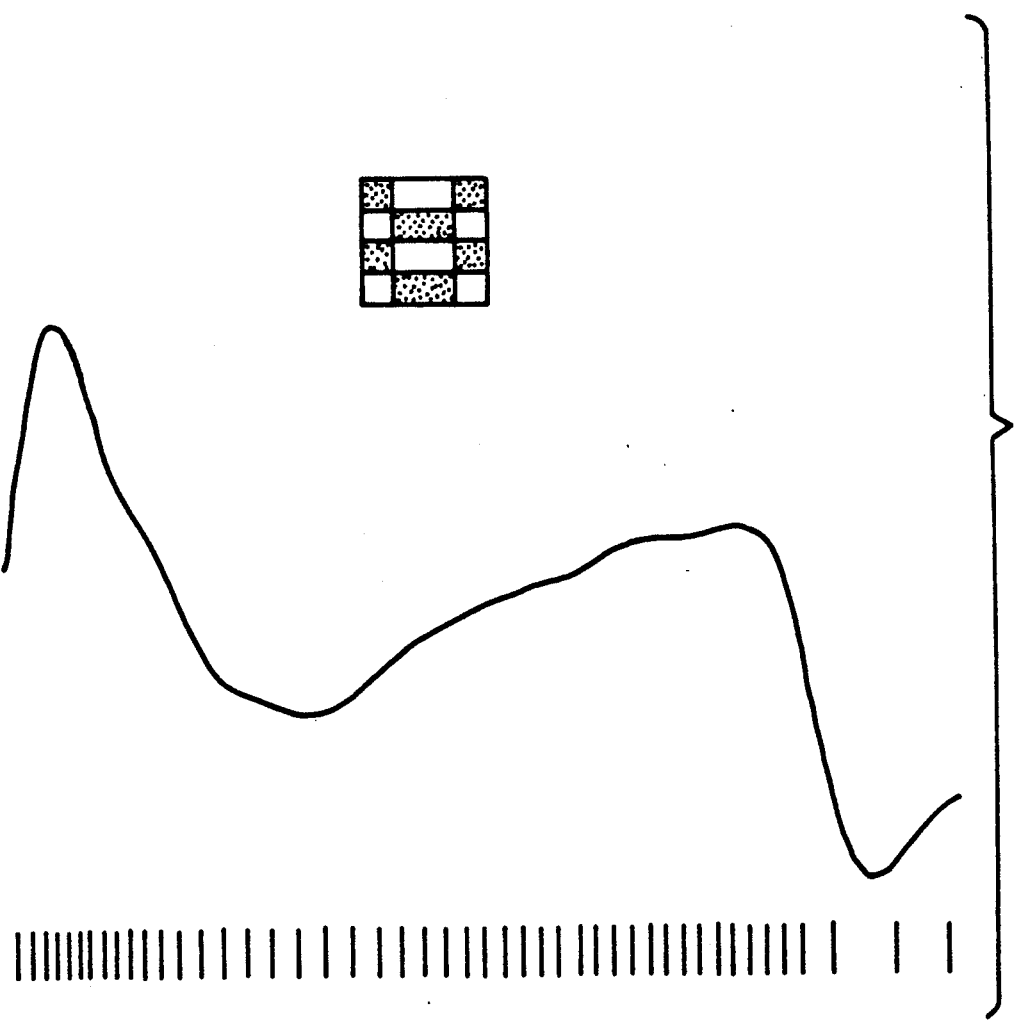
FIG. 12 is an illustration of an image pattern, its corresponding temporal encoding, and its corresponding temporally modulated spike train suitable for stimulating the visual cortex to provide a perception that is a function of the image pattern.
Figure 13:
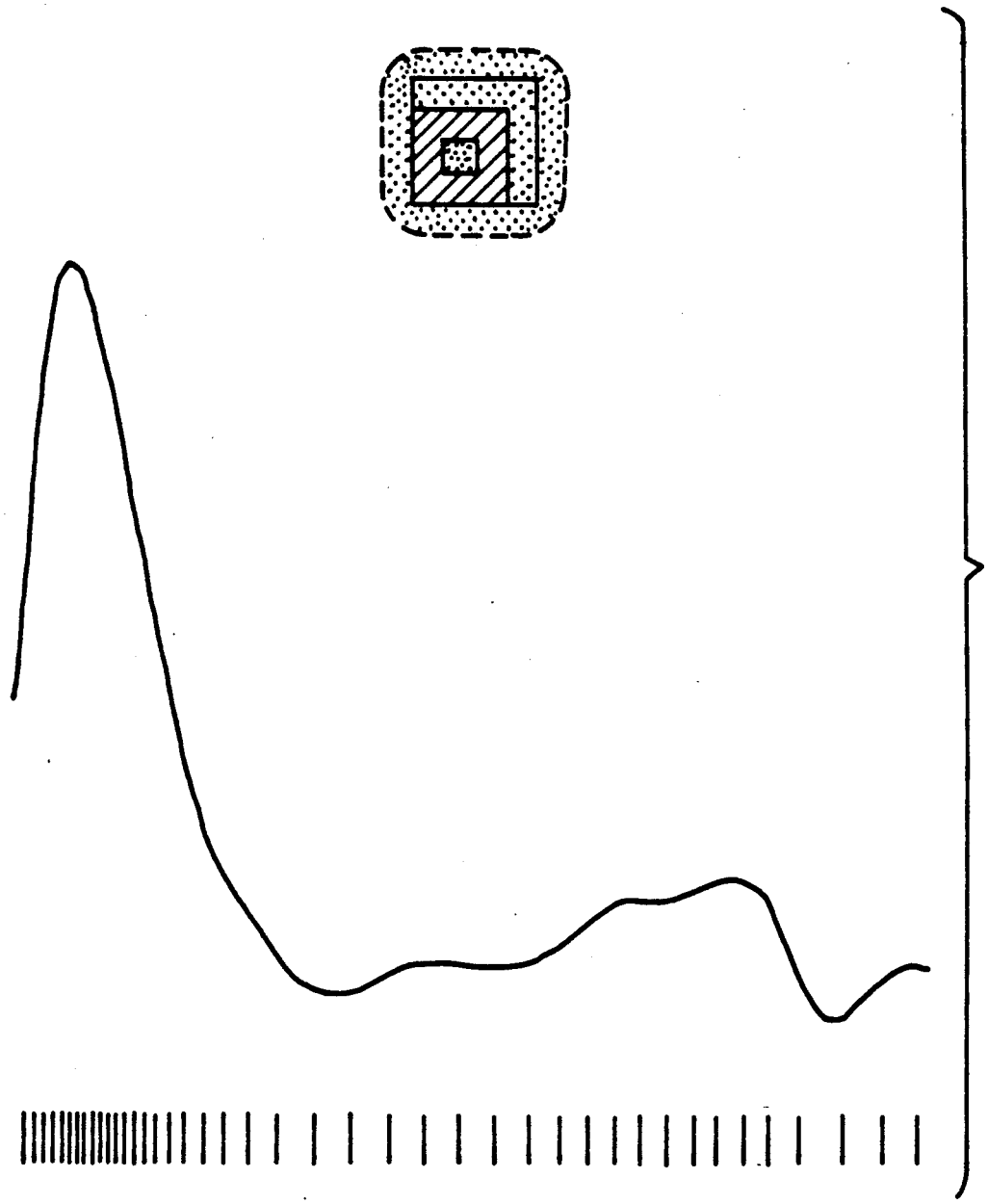
FIG. 13 is an illustration of another image pattern, its corresponding temporal encoding, and its corresponding temporally modulated spike train suitable for stimulating the visual cortex to provide a perception that is a function of the image pattern.

Exemplary temporally modulated spike trains, their corresponding waveforms, and the corresponding Walsh patterns are shown in FIGS. 12 and 13, and, as shown, the inter-spike spacing and the rate of changes thereof varies as a function of the waveform to produce a temporally modulated spike train. In practice, it has been found that inter-spike spacing varies between one and 300 milliseconds.

The present invention has been disclosed as useful in providing a simulated spike train responsive to a sensed optical image; as can be appreciated, a different input sensor, such as an array of sound-responsive devices or pressure responsive devices can likewise be utilized to provide a simulated spike train responsive to a sensed sound or pressure. The present invention advantageously allows a person to perceive environmental parameters via temporally modulated simulated neural spike trains that emulate naturally occurring spike trains in such a way that a perception based on the simulated spike train will be functionally related to the external stimuli or parameter.

As will be apparent to those skilled in the art, various changes and modifications may be made to the illustrated apparatus and method for transmitting prosthetic information to the brain of the present invention without departing from the spirit and scope of the invention as determined in the appended claims and their legal equivalent.

What is claimed is:

1. An apparatus for generating simulated neuron signals about an external stimulus sensed by a sensor that can be supplied to the brain using a neural probe comprising:

means for inputting a plurality of electrical signals produced by a sensor, the signals representative of a sensed external stimulus; and means for converting said input electrical signals into a plurality of simulated neuron signals, each simulated neuron signal containing a plurality of temporally modulated simulated neuron impulses.

2. An apparatus according to claim 1 wherein said inputting means contains a signal factor conditioner.

3. An apparatus according to claim 1 wherein said converting means comprises:
   means for weighting each electrical signal with a plurality of predetermined weighting values to produce a plurality of sets of weighted signals;
   means for summing each set of weighted signals to produce a plurality of summed signals;
   means for transforming said plurality of summed signals using a plurality of predetermined transforms into a plurality of time dependent signals;
   means for summing said plurality of time deposit signals to produce a time dependent summed output; and
   means for generating said plurality of simulated neuron impulses using said time dependent summed output.

4. An apparatus according to claim 3 wherein each of said plurality of predetermined transforms are mathematically orthogonal.

5. An apparatus according to claim 3 wherein said generating means comprises:
   means for determining a plurality of sequential amplitude values for a plurality of intervals of said time dependent summed output;
   means for adding a first sequential amplitude value to a second sequential amplitude value to obtain an added amplitude value;
   means for comparing said added amplitude value to a predetermined amplitude value; and
   pulse producing means for producing an initial simulated neuron impulse and producing a subsequent simulated neuron impulse when said comparing means determines that said added amplitude value is greater than said predetermined amplitude value.

6. An apparatus according to claim 5 further comprising:
   means for subtracting said predetermined amplitude value from said added amplitude value when said added amplitude value is greater than said predetermined amplitude value to obtain a subtracted amplitude value; and wherein said adding means adds said subtracted amplitude value and a next sequential amplitude value to obtain a subsequent added amplitude value.

7. An apparatus for generating simulated neuron signals about an external visual stimulus that can be applied to the brain using a neural probe comprising:
   means for sensing an external visual stimulus; and
   means for converting a sensed external visual stimulus into a plurality of simulated neuron signals, each simulated neuron signal containing a plurality of temporally modulated simulated neuron impulses.

8. An apparatus according to claim 7 wherein said sensing means outputs a plurality of electrical signals, each electrical signal containing information concerning a part of said sensed external visual stimulus.

9. An apparatus according to claim 8 wherein said sensing means comprises a plurality of photoreceipts arranged in an array.

10. An apparatus according to claim 8 wherein said converting means comprises:
    means for weighting each electrical signal with a plurality of predetermined weighting values to produce a plurality of sets of weighted signals;
    means for summing each set of weighted signals to produce a plurality of summed signals;
    means for transforming said plurality of summed signals using a plurality of predetermined transforms into a plurality of time dependent signals;
    means for summing said plurality of time dependent signals to produce a time dependent summed output; and
    means for generating said plurality of simulated neuron impulses using said time dependent summed output.

11. An apparatus according to claim 10 wherein each of said plurality of predetermined transforms are mathematically orthogonal.

12. An apparatus according to claim 10 wherein said generating means comprises:
    means for determining a plurality of sequential amplitude values for a plurality of intervals of said time dependent summed output;
    means for adding a first sequential amplitude value to a second sequential amplitude value to obtain an added amplitude value;
    means for comparing said added amplitude value to a predetermined amplitude value; and
    pulse producing means for producing an initial simulated neuron impulse and producing a subsequent simulated neuron impulse when said comparing means determines that said added amplitude value is greater than said predetermined amplitude value.

13. An apparatus according to claim 11 further comprising:
    means for subtracting said predetermined amplitude value from said added amplitude value when said added amplitude value is greater than said predetermined amplitude value to obtain a subtracted amplitude value; and
    wherein said adding means adds said subtracted amplitude value and a next sequential amplitude value to obtain said added amplitude value.

14. An apparatus for encoding visual information received as a plurality of electrical signals from a photodetection device into a plurality of encoded signals comprising:
    means for inputting a plurality of electrical signals representing visual information; and
    means for converting said plurality of electrical signals a plurality of encoded signals, said converting means comprising;
    means for weighting each electrical signal with a plurality of predetermined weighting values to produce a plurality of sets of weighted signals,
    means for summing each of set of weighted signals to produce a plurality of summed signals,
    means for transforming said plurality of summed signals using a plurality of predetermined transforms into a plurality of time dependent signals, and
    means for summing said plurality of time dependent signals to produce one of said encoded signals.

15. An apparatus according to claim 14 wherein each of said plurality of predetermined transforms are mathematically orthogonal.

16. A method for generating a plurality of simulated neuron signals representative of an external stimulus that can be applied to the brain using a neural probe comprising the steps of:

sensing an external stimulus; and converting the sensed external stimulus into a plurality of simulated neuron signals, each simulated neuron signal containing a plurality of temporally modulated simulated neuron impulses.

17. A method according to claim 16 wherein said sensing step further comprises sensing an external stimulus and providing a plurality of electrical signal representative of said stimulus, each electrical signal containing information representing of a point of said stimulus.

18. A method according to claim 17 wherein said converting step comprises the steps of:

weighting each electrical signal with a plurality of predetermined weighting values to produce a plurality of sets of weighted signals;

summing each set of weighted signals to produce a plurality of summed signals;

transforming said plurality of summed signals using a plurality of predetermined transforms into a plurality of time dependent signals;

summing said plurality of time dependent signals to produce a time dependent summed output; and generating said plurality of simulated neuron impulses using said time dependent summed output.

19. A method according to claim 18 wherein each of said plurality of predetermined transforms used in said transforming step are mathematically orthogonal.

20. A method according to claim 18 wherein said generating step comprises the steps of:

determining a plurality of sequential amplitude values for a plurality of intervals of said time dependent summed output;

adding a first sequential amplitude value to a second sequential amplitude value to obtain an added amplitude value;

comparing said added amplitude value to a predetermined amplitude value; and producing an initial simulated neuron impulse and producing a subsequent simulated neuron impulse when said comparing means determines that said added amplitude value is greater than said predetermined amplitude value.

21. A method according to claim 20 further including the steps of:

subtracting said predetermined amplitude value from said added amplitude value when said added amplitude value is greater than said predetermined amplitude value to obtain a subtracted amplitude value; and wherein said adding step adds said subtracted amplitude value and a next sequential amplitude value to obtain said added amplitude value.

22. A method for encoding visual information received as a plurality of electrical signals from a photodetection device into plurality of encoded signals comprising the step of:

determining values for a plurality of sets of weighing values;

determining values for a plurality of orthogonal transforms;

inputting a plurality of electrical signals representing visual information; and converting said plurality of electrical signals into a plurality of encoded signals using said weighting values and orthogonal transforms.

23. A method according to claim 22 wherein said converting step comprises the steps of:

weighting each electrical signal with said plurality of predetermined weighting values to produce a plurality of sets of weighted signals, summing each set of weighted signals to produce a plurality of summed signals, transforming said plurality of summed signals using said plurality of predetermined transforms into a plurality of time dependent signals, and summing said plurality of time dependent signals to produce one of said encoded signals.

24. An apparatus for generating simulated neuron signals about an external stimulus that can be applied to the brain using a neural probe comprising:

an array of photoreceptors for sensing said external visual stimulus, each photoreceptor producing electrical signals representative of a portion of said external visual stimulus; and means for producing a plurality of transform sum signals, one for each photoreceptor of said array, said producing means comprising:

means for storing a plurality of predetermined sets of weighting values, a plurality of multipliers, each multiplier multiplying said electrical signals and one set of said weighting values, to obtain a plurality of sets of weighted signals, a plurality of summing amplifiers, one for each set of weighted signals, for adding each set of weighted signals to obtain a plurality of summed signals, a plurality of cubic function generators, one for each summed signal, for scaling each of said summed signals to obtain a plurality of scaled signals, a plurality of sample and hold circuits, one for each scaled signal, for sampling and holding each of said plurality of scaled signals, means for storing a plurality of sets of predetermined neural transform values, a multiplexer for selecting said plurality of scaled signals, an analog to digital convertor for digitizing each of said selected sampled and held scaled signals into digitized scale signals, and a microprocessor for multiplying each of said digitized scale signal with a corresponding neural transform value to obtain transformed signals and adding these transformed signals to obtain a transform sum signal;

means for transforming said plurality of transform sum signals into a plurality of simulated neuron signals in which each simulated neuron signal contains a plurality of temporally modulated simulated neuron impulses, said transforming means comprising:

a microprocessor for adding successive interval values of said transform sum signals to obtain successive added values, a threshold register for storing a preset threshold value, a counter that produces a counter signal when said successive added values exceed said preset threshold, and a monostable multivibrator for producing one of said simulated neuron impulses.

* * * * *